Figure 1:
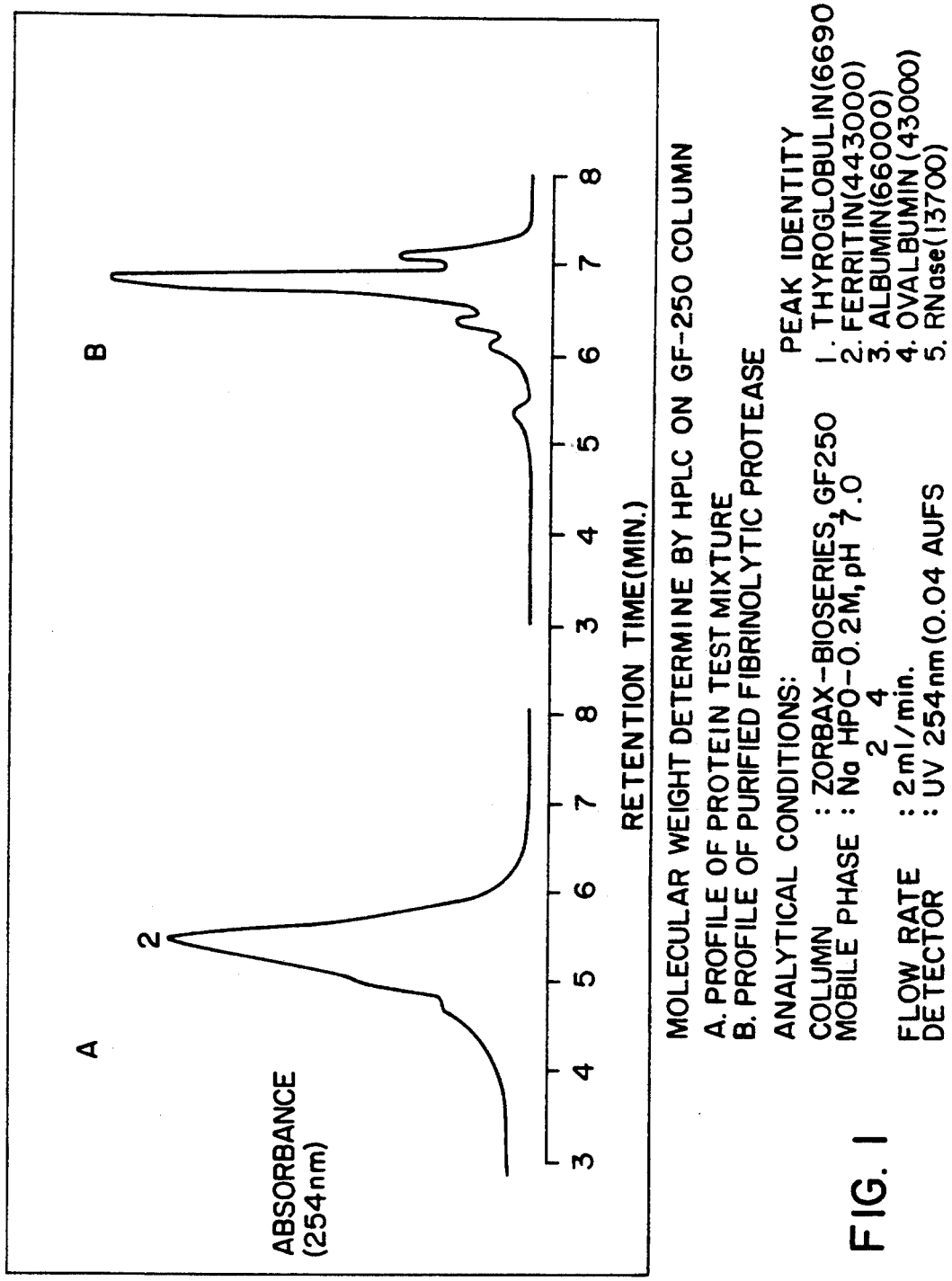
Figure 2:
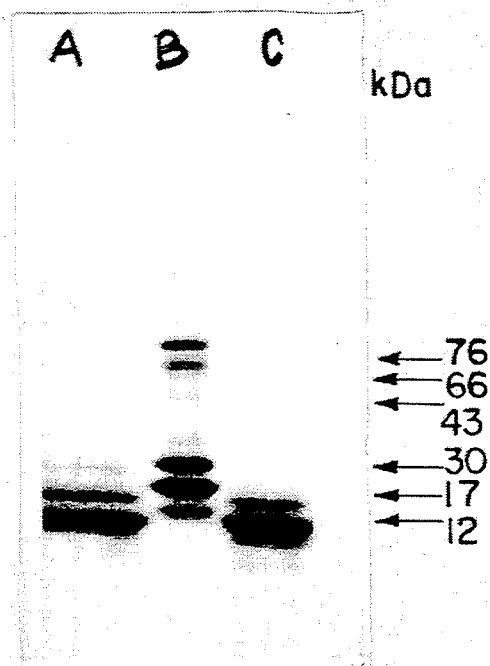
Figure 3:
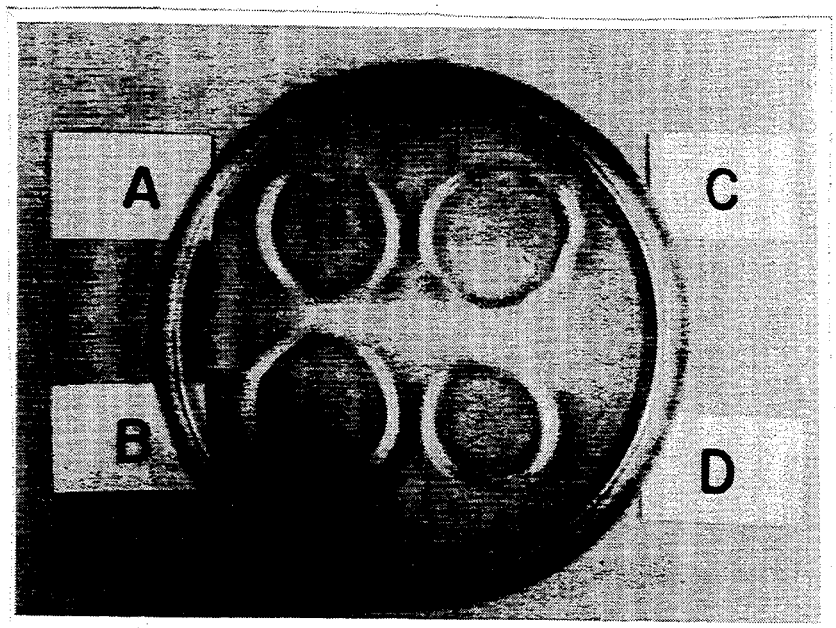

United States Patent [19]

Balaraman et al.

[11] Patent Number: 5,434,059
[45] Date of Patent: Jul. 18, 1995

[54] THROMBOLYTIC AGENT AND PROCESS OF PREPARATION THEREOF

[76] Inventors: Kothandapani Balaraman; Musavan Kuppusamy, both c/o Vector Control Research Centre, Medical Complex, Indira Nagar, Pondicherry, India, 605606

[21] Appl. No.: 119,009

[22] Filed: Sep. 9, 1993

[51] Int. Cl.6 .................. C12P 21/04; C12N 9/48; C12N 9/54
[52] U.S. Cl. .................. 435/71.2; 435/71.1; 435/71.3; 435/212; 435/217; 435/221; 435/226
[58] Field of Search .............. 435/212, 71.2, 71.3, 435/226, 71.1, 221, 217

[56] References Cited

U.S. PATENT DOCUMENTS 4,014,860  3/1977  Kakinuma et al. ............... 435/71.2
4,604,234  8/1986  Fujii et al. ............... 435/71.2
5,166,318  11/1992  Furutani et al. ............... 435/252.31

*Primary Examiner*—Herbert J. Lilling
*Attorney, Agent, or Firm*—Helfgott & Karas

[57] ABSTRACT

A process for the preparation of thrombinase. This process includes the steps of subjecting a cell free culture filtrate from a culture broth of the fermentation of *Bacillus sphaericus* serotype H5a5b to ultra filtration to obtain a SDS-PAGE PROFILE OF FIBRINOLYTIC PROTEASE FROM B. sphaericus

LANE A: CRUDE ENZYME OBTAINED AFTER AMMONIUM SULPHATE PRECIPITATION.

LANE B: MOLECULAR WEIGHT MARKER PROTEINS.

LANE C: PURIFIED ENZYME.

DETERMINATION OF FIBRINOLYTIC POTENCY.

A & C: 10 AND 20 UNITS OF STREPTOKINASE.
B & D: 20 AND 40 UL OF FIBRINOLYTIC PROTEASE FROM
B. sphaercus (1 mg PROTEIN per ml).

THROMBOLYTIC AGENT AND PROCESS OF PREPARATION THEREOF

This invention relates to a process for the preparation of thrombinase. Thrombinase is a thrombi dissolving agent containing a fibrinolytic ensyme having an advantageous application for the treatment of cerebral thrombosis, myocardial infraction, deep vein thrombosis and in the prevention of post surgical adhesion.

Streptokinase (from Streptococci) Urokinase (from human urine) and Tissue Plasminogen Activator (TPA, front human tissue culture) are the main thrombolytic agents currently known in the art. Streptokinase-aspirin combinations provide a significant relief even if the treatment is commenced 24 hrs after a heart attack. Prourokinase also known as kidney plasminogen activator is designed to dissolved clots in the blood without interfering with the body's normal blood clotting process. Beechem Laboratories clot dissolving product-anisoylated plasminogenstreptokinase activator complex, trade named, Eminase, is claimed to have reduced the death rate in heart attack victims by 50%. Gene Tech's TPA (Activase), is also highly effective in dissolving blood clots. Urokinase, Streptokinase and TPA, the first plasminogen activators available for clinical use, activate the plasminogen to active plasmin. The actual clot lysis is carried out by the active plasmin. The action of plasmin, however, is not restricted to the lysis of fibrin present in thrombus; plasmin also attacks fibrinogen and other clotting factors, which can lead to severe bleeding. Fibrinolytic potency and specificity of these agents are markedly enhanced by covalently linking them to a fibrin specific antibody. This type of targetting the fibronolytic agent to the site of thrombi opens up the possibility of using direct acting fibrinolytic enzymes in the place of plasminogen activators.

It is an object of this invention to propose a novel process for the preparation of thrombinase.

It is another object of this invention to propose such an improved process which will utilize material now discarded as waste in the known fermentation processes of *Bacillus sphaericus* serotype H5a & H5b.

It is a still further object of this invention to propose such a process which will emply the waste or discarded material in the above conventional process to produce useful chemicals as a by-product in an economical manner so that the known main fermentation itself becomes more economical and productive.

It is thus a still further object of this invention to propose an improved process for the production of biopesticide.

BRIEF DESCRIPTION OF THE DRAWINGS

FIG. 1 is a graph of molecular weight determination by HPLC on GF-250 column whereby FIG. 1A is a profile of protein test mixture and FIG. 1B is a profile of purified fibrinolytic protease.

FIG. 2 is a microphoto of the SDS-Page profile of fibrinolytic protease from *B. sphaericus* whereby in FIG. 2, Lane A is a crude enzyme obtained from ammonium sulphate precipitation, Lane B is the molecular weight marker and Lane C is the purified enzyme.

FIG. 3 is a microphoto of the Determination of fibrinolytic potency whereby FIG. 3A contains 10 units of Streptokinase, FIG. 3B contains 20 ul Fibrinolytic protease from *B. sphaericus* (1 mg. protein per ml), 3C contains 20 units of Streptokinase and FIG. 3D contains 40 ul of Fibrinolytic protease from *B. sphaericus* (1 mg. protein per ml).

In known fermentations of *Bacillus sphaericus* serotype H5a5B there is obtained a cell free culture flitrate. This is generally discarded and is thus treated as a waste.

We turned our attention to investigating the filtrate now being discarded to find out whether any valuable chemical is present therein and whether such a chemical, if any, can be economically recovered to give a by-product so as to make the main production of biopesticide economical.

We tried the effect of this filtrate on several protein sources e.g. casein and bovine serum, albumin mainly for protease activity. It was observed that ti could liquify blood clots. Further investigation indicated that it did not affect the red blood cells and acted only upon the fibrin.

This confirmed our above observations and that it is an enzyme, particularly a protease.

Attention was therefore directed into preparing a useful drug from this cell free flitrate.

From the nature of the protease identified by us, based on the known activities and published literature, we could conclude that a useful thrombolytic agent could be manufactured from this enzyme (protease).

Several investigations were carried out using different sources of the cell free filtrate and we could develop a simple physio-chemical process to manufacture the thrombolytic agent.

In general, out process comprises in subjecting the culture filtrate obtained from the main process of conventional submerged fermentation of *Bacillus sphaericus* serotype H5aH5b to simple physico chemical steps comprising ultra filtration of the cell free filtrate, concentration of the same and salting out using ammonium sulphate substantially all protein from the said cell free filtrate and decolorizing the protein in liquid medium.

Subject to paragraph (b) of 37 CFR §1.808, all of the restrictions imposed by the depository on the availability to the public of the deposited material will be irrevocably removed upon the granting of the patent.

The decolourized protein obtained can be further subjected to dialysis and lyophilization to obtain a crude powder which may be subjected to further purification.

The general process steps are illustrated in the following flow chart:

FLOW CHART OF THE PURIFICATION PROCESS OF THROMBINASE

Culture broth

↓ Removal of cells

Culture filtrate

↓ Ultrafiltration

Concentrated Retentate

↓ $(NH_4)_2SO_4$ Salt out

Ammonium sulphate Fraction

↓ Modified cellulose

-continued
FLOW CHART OF THE PURIFICATION PROCESS OF THROMBINASE

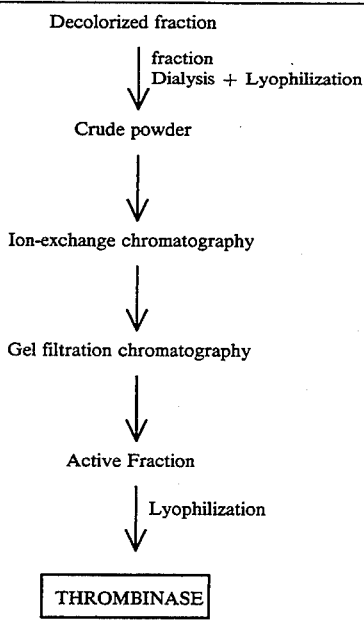

The invention will now be more fully described with reference to the following examples:

It should be noted that the salting out by using ammonium sulphate is only to change the solubility of the macromolecules of the filtrate.

We give below a Table showing the details of filtrate before it was subjected to salting out of protein and after it was subjected to salting out of protein.

TABLE I

| Sl.No. | Parameter | Before salting out | After salting out |
|---|---|---|---|
| 1. | Physical appearance of filtrate. | liquid | liquid |
| 2. | Density | 1.1 | 1.05 |
| 3. | % of solid | 0.05 | 0.05 |
| 4. | pH | 7 | 5.5 |
| 5. | colour | Dark-brown | Dark brown |

The protein that has been salted out from the filtrate is converted into an aqueous solution and then subjected to decolourization using commercially available modified cellulose such as cell debris removes supplied by Whatman or DE 52 ion exchange resin, a solid solution of an active electrolyte in a highly stable insoluble matrix, from the same manufacturer.

SUITABLE OTHER FORMS OF DE-COLOURIZATION AGENTS MAY BE STUDIED

Dialysis and Lyophiliation

These two steps are carried out in the following manner: The precipitate obtained after salting out is dissolved in water, loaded into tubular dialysing membrane bags of molecular weight cut off limit 10,000 and dialysed overnight against distilled water.

Purification of the crude powder obtained after lyophilization

The crude powder obtained is subjected to a two-stage purification.

In the first stage the powder is made into a solution with water and subjected to ion exchange treatment in the following manner: The decolorised fraction was loaded on Q-sepharose column and eluted in two steps using Tris-Hcl buffer, pH 8.0 containing 0.1M and 0.5M Na cl concentration respectively. The unbound fraction eluted with 0.1M Na cl concentration contained the fibrinolytic protease activity.

The second purification is carried out by gel filtration in the following manner: The active fraction obtained after Q-sepharose chromatography was further purified on Sephacryl-S300 column. Elution was carried out with 0.01M Tris-Hcl buffer, pH 8. Two fractions were obtained among which the second fraction contained the fibrinolytic enzyme.

Purification of the Crude Powder

Types of ion exchange used for first stage purification are to be specified and extent of purification may be stated.

Second stage purification may be made more definitive by clarifying the gel filtration, types of gel, specifications of gel, stages and final purity achieved.

Product Description

The product is a novel thrombi dissolving agent containing a fibrinolytic enzyme (Thrombinase) isolated, identified and purified for the first time from Bacillus sphaericus. This product has potential use for the treatment of Cerebral thrombosis (strock), myocerdial infarction, deep vein thrombosis and in the prevention of post surgical adhesions. The preparation can be used on its own or in combination with specific antibodies. Though the product is not a plasminogen activator, it acts very specifically on fibrin clots. The fibrinolytic action is greater than streptokinase and urokinase.

It has optimum activity in the range of 7–9 pH and is stable over the pH range 5–7.5. Molecular weight (gel filtration) was estimated to be around 18500. It is stable below 40° C. and retains 80% or more activity on standing for 24 hr at 30° C. in pH 7.2 tris-HCl buffer.

Biological activity

Assay for fibrinolytic potency

Fibrinolytic activity of the purified enzyme was evaluated in comparison to standard Streptokinase according to the modified method of Astrup and Mullertz (1952).

Fibrinolytic potency was estimated by measuring the extent of liquification (zone diameter) produced by the enzyme on fibrin clot of fibrinogen, plasminogen and thrombin at 7.5 pH and 37° C. in 15 min, Streptokinase, the reference standard was diluted to contain 500 units/ml. Thrombinase was dissolved in Tris-HCl buffer pH 7.5 $\phi$ to contain 1 mg protein/ml. Quantities of 20 and 4.0 ul of streptokinase and the test preparation were placed as a droplet on the surface of the fibrin clot and incubated at 37° C. The diameter of the digested area was measured after 30 minutes of incubation (ref. photo plate), Table 2 shows a summary of the purification of fibrinolytic protease from B. sphaericus.

TABLE 2

Summary of purification of fibrinolvtic protease from *B. sphaericus*.

| Step | | Volume (ml) | Total activity (units) | Total protein (mg) | Specific activity (units/mg) | yield (%) | purification (fold) |
|---|---|---|---|---|---|---|---|
| 1. | Culture filtrate | 40,000 | 4240000 | 88560 | 47 | 100 | 1 |
| 2. | Ultra filtration | | | | | | |
| a. | 30,000 NMWL cut (filtrates) | 38,000 | 3930000 | 72701 | 54 | 92 | 1.2 |
| b. | 10,000 NMWL cut (retentate) | 2,000 | 3250000 | 7035 | 462 | 77 | 10 |
| 3. | Ammonium sulphate fraction | 100 | 2866600 | 2580 | 1111 | 67 | 24 |
| 4. | Decolorized fraction | 100 | 2500000 | 1660 | 1506 | 59 | 32 |
| 5. | Ion exchange chromatography | 150 | 1262500 | 715 | 1765 | 30 | 38 |
| 6. | Gel filtration chromatography | 150 | 1073125 | 252 | 4258 | 25 | 91 |

Having described our invention what we claim as new is:

1. A process for the preparation of a novel thrombolytic agent which comprises obtaining a cell-free culture filtrate from the known culture broth in the fermentation of *Bacillus sphaericus* serotype H5a5b, subjecting the said cell-free culture filtrate to a step of ultra filtration in order to obtain a concentrated retentate, followed by salting out substantially all protein from the said concentrate using a salting agent, converting the salted out protein into an aqueous solution whereafter the aqueous solution is subjected to decolourization using modified cellulose, subjecting the decolourized fraction to dialysis and lyophilization to obtain a crude powder of said protein, followed by preparing a solution of crude powder and subjecting same to chromatography treatment to obtain purified material which is finally lyophilized to obtain the thrombolytic agent.

2. A process as claimed in claim 1, wherein the dialysis and lyophilization of the cellulose treated fraction is carried out by semi-permeable membrane (10000 MW cut off) and Lyophilizer, respectively to obtain crude powder of protein.

3. A process as claimed in claim 1, wherein the chromatographic treatment is carried out in two stages v.i.z. a first stage of ion exchange chromatography and a second stage of gel filtration chromatography.

4. A process as claimed in claim 5, wherein the first stage of ion exchange chromatography is carried out by subjecting a solution of the crude powder to Q Sepharose (Pharmacia Ltd, Sweden) anion exchange chromatography using 0.01M Tris-Hcl buffer, pH 8 containing 0.001M Ca $cl_2$, step wise elution was performed using the same buffer containing 0.1M Na cl and 0.5M Na cl.

5. A process as claimed in claim 3, wherein the second stage gel filtration chromatography is carried out by gel filtration on Sephacryl S-300 (Pharmacia Ltd, Sweden) using 0.05M Tris-Hcl buffer, pH 7.5 containing 0.1M Na cl.

6. A process as claimed in claim 1, wherein the dialysed positive fractions obtained through gel filtration chromatography are subjected to final lyophilization.

7. A process as claimed in claim 1, wherein the dialysed positive fractions obtained through gel filtration chromatography are subjected to final lyophilization.

8. A process as claimed in claim 1, wherein the salting agent comprises ammonium sulfate.

* * * * *